US00PP15771P2

(12) United States Plant Patent
Olesen et al.

(10) Patent No.: US PP15,771 P2
(45) Date of Patent: May 17, 2005

(54) CLIMBING ROSE PLANT NAMED 'POULYC008'

(50) Latin Name: *Rosa hybrida*
Varietal Denomination: 'POULyc008'

(75) Inventors: L. Pernille Olesen, Fredensborg (DK); Mogens N. Olesen, Fredensborg (DK)

(73) Assignee: Poulsen Roser, Fredensborg (DK)

( * ) Notice: Subject to any disclaimer, the term of this patent is extended or adjusted under 35 U.S.C. 154(b) by 0 days.

(21) Appl. No.: 10/812,760

(22) Filed: Mar. 29, 2004

(51) Int. Cl.[7] ..... A01H 5/00
(52) U.S. Cl. ..... Plt./111
(58) Field of Search ..... Plt./111

*Primary Examiner*—Kent Bell

(57) ABSTRACT

A new garden rose plant of the climber class which Has abundant, yellow-orange flowers and attractive foliage. This new and distinct variety has shown to be uniform and stable in the resulting generations from asexual propagation.

1 Drawing Sheet

Botanical classification: *Rosa hybrida.*
Variety denomination: 'POULyc008'.

SUMMARY OF THE INVENTION

The present invention constitutes a new and distinct variety of garden rose plant of the climber class, which originated from a controlled crossing between the female seed parent, an un-named seedling, and the male pollen parent 'POULurt', described and illustrated in U.S. Plant Pat. No. 9,637 dated Sep. 3, 1996. The two parents were crossed during the summer of 1992 and the resulting seeds were planted in a controlled environment in Fedensborg, Denmark. The new variety is named 'POULyc008'.

The new variety may be distinguished from its female seed parent, by the following combination of characteristics:

1. Flowers of the seed parent are more orange in color than flowers of 'POULyc008'.
2. The seed parent has larger leaves and leaflets than 'POULyc008'.

The new variety may be distinguished from its male pollen parent, 'POULurt' by the following combination of characteristics:

1. As the sepals divide, flower petals of 'POULurt' are Yellow-Orange Group 15A. Petals of 'POULyc008' are Orange-Red Group 32c to 34B.
2. While the pollen parent 'POULurt' has a petal color, upon opening, of Yellow-Orange 15A at top ½ of petal with petal fading to Yellow-Orange Group 15C at base; the same of 'POULyc008' is Orange Group 24C with intonations of Yellow Group 11B.
3. While the pollen parent 'POULurt' has a flower diameter of about 45 mm; the same characteristic of 'POULyc008' is 35 mm.

The objective of the hybridization of this rose variety was to create a new and distinct variety for garden use with unique qualities, such as:

1. Uniform and abundant yellow-orange flowers;
2. Vigorous, but compact growth when propagated both as a budded rose and on its own roots;
3. Disease resistance;

4. Reduced apical dominance in flowering habit. The new variety produces flowers evenly from the lower branches to the top of the plant.

This combination of qualities is not present in previously available commercial cultivars of this type, known to the inventors, and distinguish 'POULyc008' from all other varieties of which we are aware.

As part of their rose development program, L. Pernille Olesen and Mogens N. Olesen germinated the seeds from the aforementioned hybridization during winter of 1991 and conducted evaluations on the resulting seedlings in a controlled environment in Fredensborg, Denmark.

'POULyc008' was selected in the spring of 1992 by the inventors as a single plant from the progeny of the aforementioned hybridization.

Asexual reproduction of 'POULyc008' by traditional budding and rooted cuttings was first done by L. Pernille and Mogens N. Olesen in their nursery in Fredensborg, Denmark in July, 1992. This initial and other subsequent asexual propagations conducted in controlled environments have demonstrated that the characteristics of 'POULyc008' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULyc008'. Specifically illustrated in the drawing:

FIG. 1.1; Open flower from above, cluster of open flowers showing branching, and the attachment of leaves, buds, and peduncles;

FIG. 1.2; Flower bud closed, flower bud as sepals unfold, and partially open;

FIG. 1.3; Flower petals, detached;

FIG. 1.4; Sepals, receptacle, and peduncle;

FIG. 1.5; Juvenile leaf exhibiting anthocyanin;

FIG. 1.6; Mature leaf;

FIG. 1.7; Bare stems exhibiting thorns.

DETAILED DESCRIPTION OF THE VARIETY

The following is a description of 'POULyc008', as observed in its growth in a field nursery in Jackson County, Oreg. Observed plants are 3 years of age, and were grown on *Rosa multiflora* understock. Color references are made using The Royal Horticultural Society (London, England) Colour Chart, 1995, except where common terms of color are used.

For a comparison, several physical characteristics of the rose variety 'POULhult', a rose variety from the same inventors described and illustrated in U.S. Appl. No. 10/267,547 dated Oct. 8, 2002, are compared to 'POULyc008' in Chart 1.

CHART 1

| | 'Poulyc008' | 'Poulhult' |
|---|---|---|
| General Tonality of Open Flower | Yellow-Orange 14C | Yellow Group 11C |
| Petal Count | 25 to 30 petals | 18 to 20 petals |
| Flower Diameter | 35 mm | 55 to 60 mm |

FLOWER AND FLOWER BUD

Blooming habit: Continuous.

Flower bud:

*Size.*—Upon opening, 18 mm in length from base of receptacle to end of bud. Bud diameter is 9 mm.

*Bud form.*—Broad based pointed ovoid.

*Bud color.*—As sepals unfold, petals are Orange-Red Group 32C to 34B. At ¼ opening petals are Orange-Red Group 32C.

*Sepals.*—Upper Surface: Color: Yellow-Green Group 145B. Surface: Slightly pubescent. Lower Surface: Color: Yellow-Green Group 144B. Anthocyanic pigments the color of Greyed-Purple Group 183A observed. Texture: Smooth with medium quantity of stipitate glands. Sepal Shape: Sepal apex is cirrhose. Base is flat at union with receptacle. Sepal Margin: Margins have medium foliaceous appendages on three of the five sepals. Size: 22 mm long by 6 mm wide.

*Receptacle.*—Texture: Smooth and glaucous. Shape: Pear shaped. Size: 5 mm (h)×5 mm (w). Color: Yellow-Green Group 144A. Anthocyanic pigments the color of Greyed-Purple Group 184A observed.

*Peduncle.*—Surface: Stipitate glands is medium quantity observed. Length: 15 mm average length. Color: Yellow-Green Group 144C. Anthocyanic pigments the color of Greyed-Red Group 182A observed. Strength: Somewhat strong.

*Borne.*—Clusters of 13 to 15 flower buds per stem. Reduced apical dominance in flower habit causes flower buds to develop evenly from the base of the plant to the upper branches.

Flower bloom:

*Fragrance.*—Light floral scent.

*Duration.*—The blooms have a duration on the plant of approximately 10 to 14 days. Petals fall cleanly away from plant after flowers have fully matured.

*Size.*—Flower diameter is 35 mm when open. Flower depth is 17 mm.

*Form.*—General: Rosette. Side View: Upon opening, upper part: Flat. Upon opening, lower part: Flat. Open flower, upper part: Flat. Open flower, lower part: Concave.

Petalage: Average range is 25 to 30 petals under normal conditions with 6 petaloids.

Color:

Upon opening, petals:

*Outermost petals.*—Outer side: Orange Group 24C with intonations of Yellow Group 11B. Inner side: Yellow Group 10C.

*Innermost petals.*—Outer side: Orange Group 24C to Yellow Group 10B. Inner Side: Yellow Group 10A.

Upon opening, basal petal spots: No distinctive coloration at the petal base observed.

After opening, petals:

*Outermost petals.*—Outer side: Orange Group 24D to Yellow Group 5D. Inner Side: Yellow Group 5D.

*Innermost petals.*—Outer side: Yellow Group 5D with light intonations of Orange Group 24D. Inner Side: Yellow Group 5D.

After opening, basal petal spots: No distinctive coloration at the petal base observed.

General Tonality: On open flower Yellow-Orange Group 14C. No change in the general tonality at the end of the $14^{th}$ day. Afterwards, general tonality changes to Yellow Group 5D.

Petals:

*Petal reflex.*—Somewhat reflexed.

*Margin.*—Weak undulations of margin observed.

*Shape.*—Apex is rounded. Base is acute.

*Size.*—24 mm (l)×18 mm (w).

*Texture.*—Smooth.

*Thickness.*—Average.

*Arrangement.*—Not Formal.

Petaloids:

*Quantity.*—4 to 7.

*Shape.*—Apex is rounded. Base is acute.

*Color.*—Upper surface: Yellow Group 5D. Lower surface: Yellow Group 5D with light intonations of Orange Group 24D.

*Size.*—18 mm (l)×7 mm (w).

Reproductive organs:

*Pollen.*—None observed.

*Anthers.*—Size: 2 mm in length. Color: Yellow-Orange Group 15A. Quantity: 61 (actual count).

*Filaments.*—Color: Yellow Group 9B. Length: 4 mm.

*Pistils.*—Length: 4 mm. Quantity: 43 (actual count).

*Stigmas.*—Superior relative to the length of the filaments and the height of the anthers. Color: Yellow Group 11A.

*Styles.*—Color: Red Group 46C. Hips: None Observed in the field nursery in Jackson County, Oreg.

PLANT

Plant growth: Vigorous climbing, upright to bushy. When grown as a budded field grown plant on *Rosa multiflora* understock, the average height of the plant is 150 to 200 cm. Average spread is 90 cm.

Stems:

*Color.*—Young wood: Yellow-Green Group 144B. Older wood: Yellow-Green Group 144B.

*Surface texture.*—Young wood: Smooth. Older wood: Smooth.

Thorns:

*Incidence.*—9 thorns per 10 cm of stem.

*Size.*—Average length: 10 mm.

*Color.*—Greyed-Purple Group 185A.

*Shape.*—Deeply concave.

Plant foliage: Normal number of leaflets on normal leaves in middle of the stem: 7 leaflets.

*Compound leaf size.*—80 mm (l)×45 mm (w).

*Color.*—Mature Foliage: Upper surface is Yellow Green Group 147A to Green Group 137A. Lower surface is Yellow Green Group 146B. Juvenile foliage: Upper surface is Yellow Green Group 144A to Green Group 137A. Lower surface is Yellow Green Group 144A.

*Anthocyanin.*—Location: Rachis, margins of juvenile leaflets. Color: Greyed-Purple Group 187B.

Plant leaves and leaflets:

*Stipules.*—Size: 20 mm in length. Quantity: 2 per compound leaf. Shape: Linear, slightly broad based with outward extending apecies. Margins: Finely serrated with medium occurrence of stipitate glands. Color: Yellow-Green Group 146A.

*Petiole.*—Length: 20 mm. Color: Yellow-Green Group 146A. Observations. Few stipitate glands and thorns observed.

*Rachis.*—Length: 35 mm. Color: Yellow-Green Group 146A.

*Leaflet.*—Edge: Finely Serrated. Size: 25 to 30 mm (l)×15 to 18 mm (w). Shape: Ovate. Apex is acute to mucronate. Texture: Smooth. Thickness: Thick. Arrangement: Odd pinnate. Venation: Reticulate. Glossiness: Glossy.

Disease resistance: Above average resistance to mildew, rust, black spot, and *Botrytis* under normal growing conditions in Jackson County, Oreg.

Cold hardiness: The variety 'POULyc008' has been found to be cold tolerant to USDA Cold Hardiness Zone 6.

It is claimed:

1. A new and distinct variety of rose plant of the climber rose class named 'POULyc008', illustrated and described herein as a distinct and novel rose variety due to its abundant yellow orange flowers, exceptional flowering habit, disease resistance, and extended period of bloom.

* * * * *

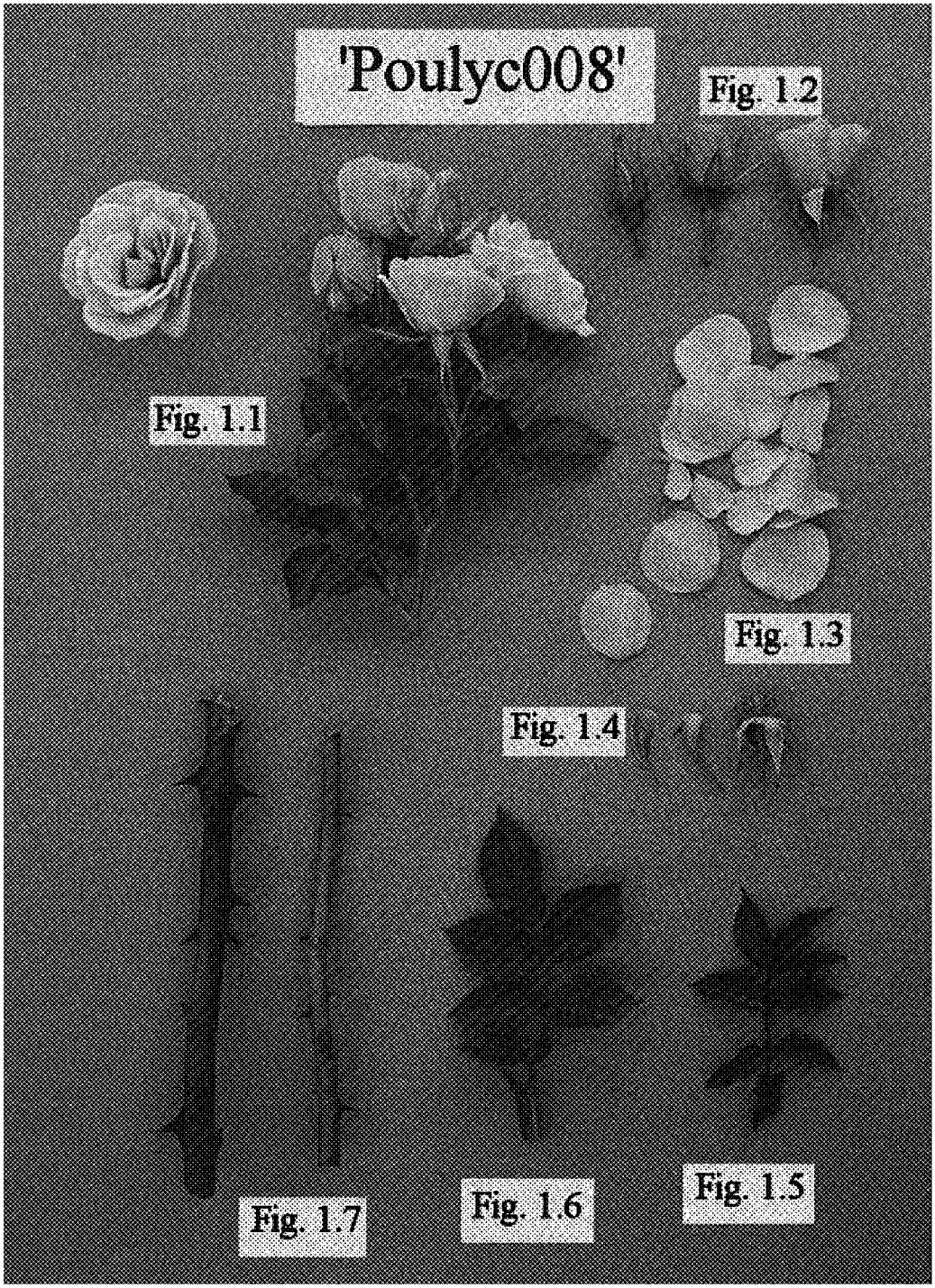
'Poulyc008'
Fig. 1.2
Fig. 1.1
Fig. 1.3
Fig. 1.4
Fig. 1.7
Fig. 1.6
Fig. 1.5